(12) United States Patent
Rizk et al.

(10) Patent No.: US 10,874,498 B2
(45) Date of Patent: Dec. 29, 2020

(54) CALENDERED SURGICAL MESHES COMPRISING POLYHYDROXYALKANOATES

(71) Applicant: Tepha, Inc., Lexington, MA (US)

(72) Inventors: Said Rizk, Windham, NH (US); Bhavin Shah, Lowell, MA (US); David P. Martin, Arlington, MA (US); Simon F. Williams, Cambridge, MA (US)

(73) Assignee: TEPHA, INC., Lexington, MA (US)

( * ) Notice: Subject to any disclaimer, the term of this patent is extended or adjusted under 35 U.S.C. 154(b) by 124 days.

(21) Appl. No.: 16/122,305

(22) Filed: Sep. 5, 2018

(65) Prior Publication Data

US 2019/0069983 A1    Mar. 7, 2019

Related U.S. Application Data

(60) Provisional application No. 62/554,673, filed on Sep. 6, 2017.

(51) Int. Cl.
*A61F 2/00* (2006.01)
*C08G 63/06* (2006.01)
(Continued)

(52) U.S. Cl.
CPC .......... *A61F 2/0063* (2013.01); *A61L 27/18* (2013.01); *A61L 27/54* (2013.01); *C08G 63/06* (2013.01);
(Continued)

(58) Field of Classification Search
CPC ........ A61F 2/0063; A61L 27/18; A61L 27/54; D01F 6/625
See application file for complete search history.

(56) References Cited

U.S. PATENT DOCUMENTS

| 5,811,272 A | 9/1998 | Snell |
| 6,245,537 B1 | 6/2001 | Williams |

(Continued)

FOREIGN PATENT DOCUMENTS

| WO | 199932536 | 1/1999 |
| WO | 9932536 | 7/1999 |

(Continued)

OTHER PUBLICATIONS

Houk, et al., "Why delta-valerolactone polymerizes and gamma-butyrolactone does not polymerize", J. Org. Chem., 2008, 73 (7):2674-2678 (2005).

(Continued)

*Primary Examiner* — Wade Miles
(74) *Attorney, Agent, or Firm* — Pabst Patent Group LLP

(57) ABSTRACT

Calendered surgical meshes comprising polyhydroxyalkanoate polymers have been developed. These meshes, preferably made from poly-4-hydroxybutyrate or copolymer thereof, have a thickness that is between 50 to 99% of the thickness of the mesh prior to calendering, and a burst strength that is not less than 20% of the burst strength of the mesh prior to calendering. The thinner calendered meshes are particularly suitable for surgical applications where a thinner profile mesh with high burst strength is required, and where it is advantageous to have a mesh with a smooth surface. The meshes may be partially or fully resorbable, and are particularly suitable for use in the treatment of pelvic organ prolapse.

20 Claims, 1 Drawing Sheet

(51) Int. Cl.
*D01F 6/62* (2006.01)
*A61L 27/18* (2006.01)
*A61L 27/54* (2006.01)
*D01D 10/00* (2006.01)

(52) U.S. Cl.
CPC ...... *D01F 6/625* (2013.01); *A61F 2002/0068* (2013.01); *A61F 2210/0004* (2013.01); *A61L 2430/34* (2013.01); *D01D 10/00* (2013.01)

(56) References Cited

U.S. PATENT DOCUMENTS

| | | | |
|---|---|---|---|
| 6,316,262 B1 | 11/2001 | Huisman | |
| 6,323,010 B1 | 11/2001 | Skraly | |
| 6,447,551 B1* | 9/2002 | Goldmann | A61F 2/0063 606/213 |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,748 B2 | 9/2003 | Clokie | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Signer | |
| 7,025,980 B1 | 4/2006 | Williams | |
| 7,179,883 B2 | 2/2007 | Williams | |
| 7,244,442 B2 | 7/2007 | Williams | |
| 7,268,205 B2 | 9/2007 | Williams | |
| 7,553,923 B2 | 6/2009 | Williams | |
| 7,618,448 B2 | 11/2009 | Schmitz | |
| 7,641,825 B2 | 1/2010 | Rizk | |
| 8,016,883 B2 | 9/2011 | Coleman | |
| 8,034,270 B2 | 10/2011 | Martin | |
| 8,039,237 B2 | 10/2011 | Martin | |
| 8,231,889 B2 | 7/2012 | Williams | |
| 8,287,909 B2 | 10/2012 | Martin | |
| 8,747,468 B2 | 6/2014 | Martin | |
| 9,457,127 B2 | 10/2016 | Martin | |
| 9,532,867 B2 | 1/2017 | Felix | |
| 9,555,155 B2 | 1/2017 | Ganatra | |
| 2010/0217392 A1* | 8/2010 | Bartee | A61L 31/048 623/16.11 |
| 2011/0189270 A1* | 8/2011 | Broom | A61L 27/54 424/451 |
| 2013/0288556 A1* | 10/2013 | Moore | D01F 6/62 442/334 |
| 2015/0313700 A1 | 11/2015 | Rizk | |
| 2015/0366669 A1* | 12/2015 | Bartee | A61F 2/0063 623/23.5 |
| 2017/0167064 A1* | 6/2017 | Taylor | D04H 1/728 |
| 2017/0231740 A1* | 8/2017 | Peery | A61B 17/064 606/151 |

FOREIGN PATENT DOCUMENTS

| | | |
|---|---|---|
| WO | 0056376 | 9/2000 |
| WO | 200056376 | 9/2000 |
| WO | 2011119742 | 9/2011 |
| WO | 2012064526 | 5/2012 |

OTHER PUBLICATIONS

Martin, et al. Medical Applications of Poly-4hydroxybutyrate: A Strong Flexible Absorbable Biomaterial, Biochem. Eng. J. 16:97-105 (2003).
Martin, et al., "Characterization of poly-4-hydroxybutyrate mesh for hernia repair applications," J. Surg. Res., 184:766-73 (2013).
Moore, et al., "Chemosynthesis of bioresorbable poly(gamma-butyrolactone) by ring-opening polymerisation: a review", Biomaterials 26:3771-3782 (2005).
Williams et al., "Poly-4-hydroxybutyrate (P4HB): a new generation of resorbable medical devices for tissue repair and regeneration", Biomed. Tech. (Berl) 58(5):439-452 (2013.
Williams, et al., "Controlled hydrolysis of poly-4-hydroxybutyrate and copolymers", Polyesters, III, 4:91-127 (2002).
International Search Report for PCT/US2018/049530.
International Search Report in PCT/US2018/049530.

* cited by examiner

| Mesh Type | Design | Courses/inch | Wales/inch |
|---|---|---|---|
| Diamond | 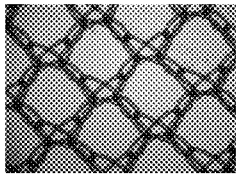 | 32 | 13 |
| Diamond Plus | 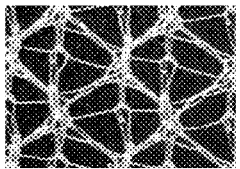 | 23 | 13 |
| Crochet | 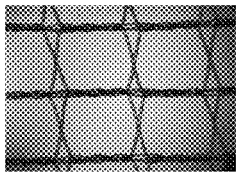 | 32 | 11 |
| Delaware | 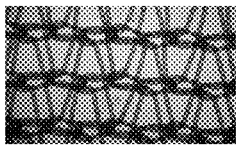 | 27 | 14 |
| Marquisette | 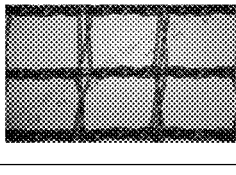 | 34 | 11 |
| Marquisette Plus | 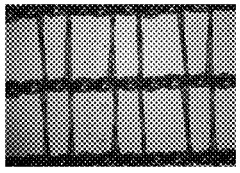 | 34 | 11 |
| Marlex | 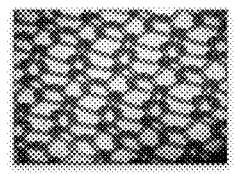 | 41 | 18 |

CALENDERED SURGICAL MESHES COMPRISING POLYHYDROXYALKANOATES

CROSS-REFERENCE TO RELATED APPLICATIONS

This application claims the benefit of and priority to U.S. Provisional Application No. 62/554,673, filed Sep. 6, 2017, which is hereby incorporated herein by reference in its entirety.

FIELD OF THE INVENTION

The present invention generally relates to calendered meshes comprising polyhydroxyalkanoates (PHAs) that are suitable for use in surgery. The meshes are partially or fully resorbable in vivo, and have high burst strengths, low profiles, and smooth surfaces that make them suitable for tissue reinforcement. The properties of the meshes are particularly useful for the surgical treatment of pelvic organ prolapse.

BACKGROUND OF THE INVENTION

Mesh products made from non-resorbable fibers, such as polypropylene and polyester, are well known in the prior art, and widely used in hernia repair. More recently, surgical meshes made from poly-4-hydroxybutyrate (P4HB) resorbable fibers have been disclosed by Martin et al. *J. Surg. Res.* 184:766-773 (2013), and are now also used in the clinic, for example, in hernia repair and mastopexy. However, these meshes are not ideally suited for all applications where the use of surgical mesh for tissue reinforcement is desirable because of surface roughness and a relatively thick profile. For example, in the surgical treatment of pelvic organ prolapse it would be desirable to have meshes that are smoother, create less friction when in contact with tissues, and have a thinner profile.

Thus, there is a need to develop surgical meshes with smoother surfaces and thinner profiles, but with burst strengths comparable to existing surgical meshes. Ideally, these meshes should be resorbable, provide a scaffold for tissue in-growth, and degrade once sufficient tissue is present to provide a strong repair.

It is an object of the present invention to provide surgical meshes comprising polyhydroxyalkanoates that have been calendered so that they have smooth surfaces, thin profiles, yet retain high burst strengths.

It is a further object of the present invention to provide calendered surgical meshes comprising polyhydroxyalkanoates where the pore sizes are not less than 40% of the pore size of the mesh prior to calendaring.

It is yet a further object of the present invention to provide methods to prepare the calendered surgical meshes comprising polyhydroxyalkanoates.

It is still a further object of the present invention to provide methods to implant the calendered surgical meshes.

SUMMARY OF THE INVENTION

Calendered surgical meshes made from polyhydroxyalkanoates have been developed. The surgical meshes have smooth surfaces, thin profiles, yet retain high burst strengths. The thinner calendered meshes are particularly suitable for surgical applications where a thinner profile mesh with high burst strength is required, and where it is advantageous to have a mesh with a smooth surface. The meshes may be partially or fully resorbable, allow tissue in-growth, and are particularly suitable for use in tissue reinforcement applications such as the treatment of pelvic organ prolapse. In the preferred embodiment, the surgical meshes are made from poly-4-hydroxybutyrate, and have a burst strength that is not less than 20% of the burst strength of the mesh prior to calendering, and a thickness that is between 50 to 99% of the thickness of the mesh prior to calendering.

BRIEF DESCRIPTION OF THE DRAWINGS

FIG. 1 is a diagram of Diamond, Diamond Plus, Crochet, Delaware, Marquisette, Marquisette Plus and Marlex mesh constructions made from P4HB monofilament fiber that have been calendered.

DETAILED DESCRIPTION OF THE INVENTION

Methods have been developed to prepare surgical meshes that have smooth surfaces, thinner profiles, and yet have high burst strengths. The meshes have pore sizes that allow tissue in-growth, and are preferably made from resorbable polymers that allow reinforcement at the surgical site with the reinforcement transitioning from support by the mesh to support by tissue that grows into the mesh as the mesh degrades. The surgical meshes are particularly useful when it is desirable to implant a resorbable mesh with high burst strength that does not have a rough surface. For example, the surgical meshes are particularly useful for the treatment of pelvic organ prolapse where surgical meshes with rough, abrasive surfaces are not desirable.

The surgical meshes are preferably made from resorbable polymers, preferably polyhydroxyalkanoate polymers (PHA polymers) and even more preferably from poly-4-hydroxybutyrate and copolymers thereof. The meshes made by the new methods have very different surface properties to surgical meshes previously produced due to the lower profiles of the fibers where they overlap in the knitted and woven constructions. For example, in a knitted mesh, the fiber protrudes less from the plane of the mesh in the vicinity of the interlocking loops, or protrudes less from the mesh plane in a woven mesh structure.

The surgical meshes feel smoother and are less abrasive in contact with tissues because there is less protrusion of fiber bundles, knots, loops or weaves from the plane of the mesh. In addition to their smoother surfaces and high burst strengths, the meshes produced by the new method have pore sizes that are still large enough to allow tissue in-growth, and suture pullout strengths that are still high enough to anchor the meshes to tissues without tearing of the meshes.

The methods disclosed herein are based upon the discovery that surgical meshes of P4HB and copolymers thereof can be calendered to make their surfaces smoother, without significant loss of burst strength, suture pullout strength or reduction in pore size. In a preferred embodiment, the methods allow mesh made with oriented P4HB fiber to be calendered without significant loss of fiber orientation using pressure, and optionally heat.

I. Definitions

"Aerial density" as used herein is measured by cutting a sample of mesh with dimensions of 2 square inches, weighing the sample, and multiplying the value by 388. The result is reported in gram/m$^2$.

"Bioactive agent" is used herein to refer to therapeutic, prophylactic, and/or diagnostic agents. These include physiologically or pharmacologically active substances that act locally or systemically in the body. A biologically active agent is a substance used for, for example, the treatment, prevention, diagnosis, cure, or mitigation of one or more symptoms or characteristics of a disease or disorder, a substance that affects the structure or function of the body, or pro-drugs, which become biologically active or more active after they have been placed in a predetermined physiological environment. Bioactive agents include biologically, physiologically, or pharmacologically active substances that act locally or systemically in the human or animal body. Examples can include, but are not limited to, small-molecule drugs, peptides, proteins, sugars, polysaccharides, nucleotides, oligonucleotides, and nucleic acid molecules such as aptamers, siRNA, miRNA and combinations thereof.

"Biocompatible" as generally used herein means the biological response to the material or device is appropriate for the device's intended application in vivo. Metabolites of these materials should also be biocompatible.

"Blend" as generally used herein means a physical combination of different polymers, as opposed to a copolymer comprised of two or more different monomers.

"Burst strength" as used herein is determined by test method ASTM D6797-02 "Standard test method for bursting strength of fabrics constant rate of extension (CRE) ball burst test," using a MTS Q-Test Elite universal testing machine or similar device. The testing fixture uses a ⅜-inch diameter ball.

"Calendering" as used herein is a process of applying pressure, and optionally heat, by means of calenders, in order to reduce the thickness of the mesh.

"Copolymers of poly-4-hydroxybutyrate" as generally used herein means any polymer having 4-hydroxybutyrate with one or more different hydroxyalkanoic acid units.

"Elongation" or "extensibility" of a material means the amount of increase in length resulting from, as an example, the tension to break a specimen. It is expressed usually as a percentage of the original length. (Rosato's Plastics Encyclopedia and Dictionary, Oxford Univ. Press, 1993).

"Molecular weight" as used herein, unless otherwise specified, refers to the weight average molecular weight (Mw), not number average molecular weight (Mn), and is measured by gel permeation chromatography (GPC) relative to polystyrene.

"Polyhydroxyalkanoates" or "PHAs" are linear polyesters produced by bacterial fermentation. Depending upon the microorganism and the cultivation conditions, homo- or copolyesters with different hydroxyalkanoic acids are generated.

"Poly-4-hydroxybutyrate" as used herein means a homopolymer having 4-hydroxybutyrate units. It may be referred to herein as P4HB, Tepha's P4HB™ polymer, or TephaFLEX® biomaterial (manufactured by Tepha, Inc., Lexington, Mass.). Polyhydroxybutyrate as generally used in the literature refers to the naturally occurring polymer poly-3-hydroxybutyrate.

"Pore size" as generally used herein is calculated using open source ImageJ software available at https://imagej.nih.gov/ij/index.html.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body within five years, whether degradation is due mainly to hydrolysis or mediated by metabolic processes.

"Stiffness" as used herein is determined by test method ASTM D4032-08 "Standard test method for stiffness of fabric by the circular bend procedure" using an Instron Tensile Tester with 10 N load cell, sample size of 1.5 in×1.5 in, ramp rate of 16 mm/s, plunger diameter of 10 mm with hemispherical tip, bore size of 16 mm, and bore plate thickness of ¼ in.

"Surface area ratio" as used herein is calculated from the following equation: surface area ratio=(π×fiber diameter× length of fiber per unit area).

"Suture pullout strength" as used herein means the peak load (kg) at which an implant fails to retain a suture. It is determined using a tensile testing machine by securing an implant in a horizontal holding plate, threading a suture in a loop through the implant at a distance of 1 cm from the edge of the implant, and securing the suture arms in a fiber grip positioned above the implant. Testing is performed at a crosshead rate of 100 mm/min, and the peak load (kg) is recorded. The suture is selected so that the implant will fail before the suture fails. The suture pullout strength may be converted and expressed as Newtons.

"Tensile modulus" is the ratio of stress to strain for a given material within its proportional limit.

II. Compositions

Methods have been developed to produce calendered surgical meshes from PHA compositions that have smooth surfaces, thin profiles, and yet retain high burst strengths. The meshes have adequate pore sizes to allow tissue ingrowth, and are particularly suitable for use in tissue reinforcement applications such as the treatment of pelvic organ prolapse where it is desirable to minimize friction of the mesh on tissue surfaces.

A. Polymers

The methods described herein can typically be used to produce calendered surgical meshes from polyhydroxyalkanoate polymers, and more preferably from poly-4-hydroxybutyrate (Tepha's P4HB™ polymer) or a copolymer thereof. Copolymers include 4-hydroxybutyrate with 3-hydroxybutyrate, 4-hydroxybutyrate with glycolic acid monomer, and 4-hydroxybutyrate with lactic acid monomer. P4HB and copolymers thereof can be obtained from Tepha, Inc. of Lexington, Mass. Preferred PHA polymers, including P4HB, have a weight average molecular weight (Mw) of 50,000 to 1,200,000, preferably 100,000 to 1,000,000 and more preferably, 100,000 to 800,000 Daltons based on gel permeation chromatography (GPC) relative to polystyrene standards.

Polyhydroxyalkanoates (PHAs) are produced by numerous microorganisms (see, for example, Steinbüchel A., et al. Diversity of Bacterial Polyhydroxyalkanoic Acids, *FEMS Microbial. Lett.* 128:219-228 (1995)). In nature, these polyesters are produced as storage granules inside cells, and serve to regulate energy metabolism. They are also of commercial interest because of their thermoplastic properties, and relative ease of production.

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). P4HB is not naturally occurring. Poly-4-hydroxybutyrate (Tepha's P4HB™ polymer, Tepha- FLEX® biomaterial) is a strong, pliable thermoplastic polyester that, despite its biosynthetic route, has a relatively simple structure. Chemical synthesis of P4HB has been attempted, but it has been impossible to produce the polymer with a sufficiently high molecular weight that is necessary for most applications, including melt processing (see Hori, et al., *Polymer* 36:4703-4705 (1995); Houk, et al., *J. Org. Chem.*, 2008, 73 (7), 2674-2678; and Moore, et al., *Biomaterials* 26:3771-3782 (2005)). In fact, it has been calculated to be thermodynamically impossible to chemically synthesize a high molecular weight homopolymer under normal conditions (Moore, et al., *Biomaterials* 26:3771-3782 (2005)). Chemical synthesis of P4HB instead yields short chain oily oligomers that lack the desirable thermoplastic properties of the high molecular weight P4HB polymers produced by biosynthetic methods.

It should be noted that the literature commonly refers to another polyhydroxyalkanoate, poly-3-hydroxybutyrate (P3HB), simply as polyhydroxybutyrate (PHB) (see Section 2 of Moore, et al., *Biomaterials* 26:3771-3782 (2005)). PHB has entirely different properties to P4HB. It is structurally and functionally different to P4HB. For example, PHB has a melting point of 180° C. versus a melting point of about 61° C. for P4HB. The polymers also have substantially different glass transition temperatures and mechanical properties. For example, PHB is a relatively hard brittle polymer with an extension to break of just a few percent, whereas P4HB is a strong extensible polymer with an extension to break of about 1,000%. Substantially different conditions are required to process these two polymers, and the resulting products have substantially different properties.

U.S. Pat. Nos. 6,245,537, 6,623,748, 7,244,442, and 8,231,889 describe methods of making PHAs with little to no endotoxin, which are suitable for medical applications. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Copolymers of P4HB include 4-hydroxybutyrate copolymerized with 3-hydroxybutyrate, glycolic acid (U.S. Pat. No. 8,039,237 to Martin and Skraly, U.S. Pat. No. 6,316,262 to Huisman et al., and U.S. Pat. No. 6,323,010 to Skraly et al.) and lactic acid. Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III*, 4:91-127 (2002), Martin, D. et al. Medical Applications of Poly-4-hydroxybutyrate: A Strong Flexible Absorbable Biomaterial, *Biochem. Eng. J.* 16:97-105 (2003), and Williams, S. et al. Poly-4-hydroxybutyrate (P4HB): a new generation of resorbable medical devices for tissue repair and regeneration, *Biomed. Tech. (Berl)* ISSN (Online) 1862-278X, ISSN (Print) 0013-5585, DOI: 10.1515/bmt-2013-0009, 2013. Medical devices and applications of P4HB have also been disclosed by WO 00/56376 to Williams et al. Several patents including U.S. Pat. Nos. 6,555,123, 6,585,994, and 7,025,980 to Williams and Martin describe the use of PHAs in tissue repair and engineering. WO 2007/092417 to Rizk et al. discloses compositions of PLA (polylactic acid) toughened with P4HB suitable for medical applications.

U.S. Pat. No. 8,034,270 to Martin et al., U.S. Pat. No. 8,016,883 to Coleman et al., U.S. Pat. No. 8,287,909 to Martin et al., U.S. Pat. No. 8,747,468 to Martin et al., U.S. Pat. No. 9,532,867 to Felix, and U.S. Pat. No. 9,555,155 to Ganatra, and US Patent Application No. 2015/0313700 to Rizk disclose textiles made by melt extrusion of P4HB. However, none of these disclosures describe a calendered surgical mesh having a PHA or P4HB monofilament mesh. These disclosures do not describe the processes that would be necessary to form such products, including methods to produce calendered mesh without de-orientation of the P4HB monofilament fiber, methods to produce smoother mesh surfaces using calendering, methods to prevent substantial loss of burst strength and suture pullout strength during calendering, and methods to prevent reduction in pore sizes that would prevent tissue in-growth during calendering.

If desired, the PHA polymer may be blended with another PHA polymer prior to processing, or blended with a non-PHA material, including other absorbable biocompatible polymers, dyes and bioactive agents (such as drug molecules or other therapeutic, prophylactic or diagnostic agents). Other absorbable biocompatible polymers in any form, including fibers and coatings, may also be incorporated into the surgical meshes to form hybrid structures. Other absorbable biocompatible polymers, include, but are not limited to, poly(lactides); poly(glycolides); poly(lactide-co-glycolides); poly(lactic acid); poly(glycolic acid); poly(lactic acid-co-glycolic acids); polycaprolactones; poly(orthoesters); polyanhydrides; poly(phosphazenes); synthetically or biologically prepared polyesters (including polyesters with one or more of the following monomeric units: glycolic, lactic; trimethylene carbonate, p-dioxanone, or ε-caprolactone); poly(lactide-co-caprolactones); polycarbonates; tyrosine polycarbonates; polyamides (including synthetic and natural polyamides, polypeptides, and poly(amino acids)); polyesteramides; poly(dioxanones); poly(alkylene alkylates); polyethers (such as polyethylene glycol, PEG, and polyethylene oxide, PEO); polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); chitin; chitosan; modified chitosan; collagen; silk; biocompatible polysaccharides; biocompatible copolymers (including block copolymers or random copolymers); hydrophilic or water soluble polymers, such as polyethylene glycol, (PEG) or polyvinyl pyrrolidone (PVP), with blocks of other biocompatible or biodegradable polymers, for example, poly (lactide), poly(lactide-co-glycolide), or polycaprolactone or combinations thereof. In some embodiments, the implant includes hyaluronic acid or derivative thereof, collagen, hydroxyapatite, or absorbable polymer having one or more of the following monomeric units: glycolic acid, lactic acid, trimethylene carbonate, p-dioxanone, and caprolactone.

In one embodiment, the calendered surgical meshes include one or more of the following: dye, medical marker, contrast agent, radiopaque marker, radioactive substance.

B. Additives

Certain additives may be incorporated into PHAs, including P4HB, copolymers and blends thereof prior to converting these compositions into calendered surgical meshes. Preferably, these additives are incorporated during the compounding process to produce pellets that can be subsequently processed into fibers suitable for making the calendered surgical meshes. In another embodiment, the additives may be incorporated using a solution-based process. In a preferred embodiment, the additives are biocompatible, and even more preferably the additives are both biocompatible and resorbable.

In one embodiment, the additives may be nucleating agents and/or plasticizers. These additives may be added in sufficient quantity to produce the desired result. In general, these additives may be added in amounts of up to 20% by weight. Nucleating agents may be incorporated to increase the rate of crystallization of the P4HB homopolymer, copolymer or blend. Such agents may be used to improve the mechanical properties of fibers and meshes, and to reduce cycle times. Preferred nucleating agents include, but are not limited to, salts of organic acids such as calcium citrate, polymers or oligomers of PHA polymers and copolymers, high melting polymers such as PGA, talc, micronized mica, calcium carbonate, ammonium chloride, and aromatic amino acids such as tyrosine and phenylalanine.

Plasticizers that may be incorporated into the compositions include, but are not limited to, di-n-butyl maleate, methyl laureate, dibutyl fumarate, di(2-ethylhexyl) (dioctyl) maleate, paraffin, dodecanol, olive oil, soybean oil, polytetramethylene glycols, methyl oleate, n-propyl oleate, tetrahydrofurfuryl oleate, epoxidized linseed oil, 2-ethyl hexyl epoxytallate, glycerol triacetate, methyl linoleate, dibutyl fumarate, methyl acetyl ricinoleate, acetyl tri(n-butyl) citrate, acetyl triethyl citrate, tri(n-butyl) citrate, triethyl citrate, bis(2-hydroxyethyl) dimerate, butyl ricinoleate, glyceryl tri-(acetyl ricinoleate), methyl ricinoleate, n-butyl acetyl ricinoleate, propylene glycol ricinoleate, diethyl succinate, diisobutyl adipate, dimethyl azelate, di(n-hexyl) azelate, tri-butyl phosphate, and mixtures thereof. Particularly preferred plasticizers are citrate esters.

In another preferred embodiment, the additives are contrast agents, radiopaque markers and radioactive substances. These additives may also be incorporated into the P4HB homopolymer, copolymer or blend either before preparing fibers that are processed into calendered surgical meshes or after they are prepared.

C. Bioactive Agents

If desired, the PHA polymer, including P4HB homopolymer and copolymers thereof, used to make the calendered surgical meshes may incorporate bioactive agents. These bioactive agents may be added during the formulation process, during pelletization or blending, or may be added later to the fibers or meshes. The bioactive agents may be contained in the polymer or copolymer or coated on the surface, or both.

In one embodiment, the bioactive agents, the PHA or preferably the P4HB polymer, copolymer, or blend, may be dissolved in a solvent or solvent system in order to disperse the bioactive agent in the PHA or P4HB polymer, copolymer or blend, and the solvent may then be removed by evaporation. Preferred solvents for P4HB include methylene chloride, chloroform, tetrahydrofuran, acetone, dimethylformamide, and 1,4-dioxane.

Examples of bioactive agents that can be incorporated into the PHA or preferably the P4HB polymer, copolymer, or blends thereof, include, but are not limited to, small-molecule drugs, anti-inflammatory agents, immunomodulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, platelet rich plasma, anesthetics, hormones, antibodies, growth factors, extracellular matrix or components thereof (fibronectin, laminin, vitronectin), integrins, antibiotics, steroids, hydroxyapatite, silver particles, vitamins, non-steroidal anti-inflammatory drugs, chitosan and derivatives thereof, alginate and derivatives thereof, collagen, hyaluronic acid and derivatives thereof, allograft material, xenograft material, and ceramics. Representative materials include proteins, peptides, sugars, polysaccharides, nucleotides, oligonucleotides, lipids, lipoproteins, nucleic acid molecules such as antisense molecules, aptamers, siRNA, and combinations thereof.

In an embodiment, the bioactive agent is an antimicrobial. Antimicrobial agents that may be incorporated into the calendered PHA meshes, more preferably P4HB mesh, include, but are not limited to, antibacterial drugs, antiviral agents, antifungal agents, and antiparisitic drugs. Antimicrobial agents include substances that kill or inhibit the growth of microbes such as microbicidal and microbiostatic agents. Antimicrobial agents that may be incorporated into the calendered PHA meshes, include, but are not limited to: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes. In a preferred embodiment, the antimicrobial agents incorporated into the calendered PHA meshes are (i) rifampin and (ii) minocycline and its hydrochloride, sulfate, or phosphate salt. In a particularly preferred embodiment, the calendered PHA meshes comprise rifampin and minocycline or its hydrochloride, sulfate, or phosphate salt.

III. Calendered Surgical PHA Meshes and Methods of Manufacturing

A. Fibers for Making Calendered PHA Surgical Meshes

In a preferred embodiment, the calendered surgical meshes are formed from P4HB monofilament meshes. The P4HB monofilament fibers used to make these meshes may be prepared in one embodiment by melt extrusion or in another embodiment by solution spinning. In a preferred embodiment, the P4HB monofilament fibers are made by melt extrusion, for example, as described by WO 2011/119742 to Martin et al., U.S. Pat. No. 8,034,270 to Martin et al., and U.S. Pat. No. 9,555,155 to Ganatra et al.

The diameters of the P4HB monofilament fibers may range from 10 µm to 1 mm, but more preferably have a diameter ranging from 50 µm to 600 µm, and even more preferably from 50 µm to 250 µm, including diameters of 10, 20, 30, 40, 50, 60, 70, 80, 90, 100, 110, 120, 130, 140, 150, 160, 170, 180, 190, 200, 210, 220, 230, 240 and 250 µm. In a particularly preferred embodiment, the P4HB monofilament fibers have a diameter of 80 µm to 125 µm, and more preferably 100 µm. In a preferred embodiment, the P4HB monofilament fibers are oriented. The exact mechanical properties of the fibers will depend upon the degree of orientation. In a particularly preferred embodiment, the oriented P4HB monofilament fibers will have one or more of the following properties: a tensile strength of at least 100 MPa, more preferably at least 300 MPa, and even more preferably at least 500 MPa, but less than 1,500 MPa, including 100, 200, 300, 400, 500, 600, 700, 800, 900, 1,000, 1,100, 1,200, 1,300, 1,400 and 1,500 MPa; an elongation to break of less than 1,100%, more preferably less than 500%, and even more preferably less than 100%, but greater than 10%, including 10, 20, 30, 40, 50, 60, 70, 80, 90, 100, 200, 300, 400, 500, 600, 700, 800, 900, 1,000 and 1,100%; a tensile modulus of at least 70 MPa, more preferably at least 300 MPa, and even more preferably at least 500 MPa, but less than 2 GPa, including 70, 80, 90, 100, 200, 300, 400, 500, 600, 700, 800, 900, 1,000, 1,100, 1,200, 1,300, 1,400, 1,500, 1,600, 1,700, 1,800, 1,900 and 2,000 MPa. In a preferred embodiment, the P4HB fibers have been prepared by stretching unoriented fibers by 6-11×.

In another embodiment, the calendered surgical meshes comprise P4HB multifilament fibers that are oriented or un-oriented, as well as P4HB monofilament fibers. P4HB multifilament fibers may be prepared by melt extrusion or solution spinning. In a preferred embodiment, the P4HB multifilament fibers are made by melt extrusion, and may be prepared as described by WO 2011/119742 to Martin et al., U.S. Pat. No. 8,034,270 to Martin et al, and U.S. Pat. No. 9,555,155 to Ganatra. In an embodiment, the P4HB multifilament fibers are prepared with a denier per filament (dpf) between 1.5 and 12.

B. Properties of Calendered PHA Meshes

In an embodiment, the calendered PHA meshes have one or more of the following properties: a suture pullout strength between 1 N and 100 N, more preferably between 5 N and 50 N, and even more preferably between 7 N and 40 N; a burst strength between 30 N and 300 N, more preferably between 50 N and 275 N, and even more preferably between 60 N and 250 N; a burst strength that is not less than 80% of the burst strength of the PHA mesh prior to calendering; a pore size between 0.05 mm² and 10 mm², more preferably between 0.05 mm² and 8 mm², and even more preferably between 0.75 mm² and 6 mm²; a pore size that is not less than 40%, more preferably not less than 30%, and even more preferably not less than 20% of the pore size of the PHA mesh prior to calendering; a thickness between 0.05 mm and 5 mm, more preferably between 0.1 mm and 1 mm, and even more preferably between 0.2 mm and 0.7 mm; a thickness that is between 50 to 99%, more preferably 50% to 85%, and even more preferably 50% to 80% of the PHA mesh thickness prior to calendering; a stiffness between 0.01 N and 5 N, more preferably between 0.1 N and 2 N, and even more preferably between 0.4 N and 1.8 N; an areal density between 5 gm/m² and 250 g/m², more preferably between 10 g/m² and 100 g/m², and even more preferably between 40 g/m² and 100 g/m²; a surface area ratio of between 0.5 cm²/cm² and 5 cm²/cm², and more preferably between 1 cm²/cm² and 4 cm²/cm²; a tensile strength in the machine direction (MD) between 5 N and 200 N, more preferably between 7 N and 100 N; a tensile strength in the cross machine direction (CMD) between 5 N and 100 N, more preferably between 10 N and 60 N; between 10 and 100 courses per inch, preferably between 20 and 50 courses per inch, more preferably between 25 and 45 courses per inch; and between 10 and 100 wales per inch, preferably 10 and 50 wales per inch, more preferably between 10 and 20 wales per inch.

In a preferred embodiment, the calendered PHA mesh is made from P4HB monofilament fiber, more preferably oriented P4HB monofilament fiber. In a more preferred embodiment, the calendered P4HB monofilament mesh has a knitted or woven structure.

In another embodiment, the calendered PHA meshes may comprise different sized fibers or other non-PHA fibers, including PHA multifilament, and fibers made from other absorbable or non-absorbable biocompatible polymers and hybrid meshes.

In an embodiment, the calendered PHA meshes are three-dimensional and can be temporarily deformed to facilitate implantation. In some embodiments, the calendered PHA meshes can be contoured to fit a patient's tissue or they can be shaped into a plug, wad, stopper, seal, or wedge.

C. Manufacture of PHA Meshes Suitable for Calendering

In a preferred embodiment, the calendered surgical meshes comprise P4HB monofilament meshes. In one embodiment, P4HB monofilament meshes that can be calendered may be made as disclosed by WO 2011/119742 and U.S. Pat. Nos. 8,034,270 and 8,747,468 to Martin et al. and U.S. Pat. No. 9,555,155 to Ganatra et al.

In one embodiment, the P4HB monofilament meshes suitable for calendering are warp knit meshes. The construction of the warp knit meshes that can be calendered are not limited to any particular design, however, preferred warp knit meshes include the Diamond, Diamond Plus, Crotchet, Delaware, Marquisette, Marquisette Plus and Marlex mesh constructions shown in FIG. 1.

In another embodiment, the P4HB monofilament meshes suitable for calendering are crotcheted. Examples of meshes that have been crotcheted are shown in FIG. 1 (see Crotchet, Marquisette and Marquisette Plus as examples of crotcheted constructions).

In yet another embodiment, the P4HB monofilament meshes suitable for calendering are woven.

A warp knit P4HB Marlex mesh suitable for calendering may be prepared using the following procedure. Spools with P4HB monofilament fiber are converted into P4HB monofilament mesh as follows: Monofilament fibers from 49 spools are mounted on a creel, aligned side by side and pulled under uniform tension to the upper surface of a "kiss" roller. The "kiss" roller is spun while semi-immersed in a bath filled with a 10% solution of TWEEN® 20 lubricant. The TWEEN® 20 lubricant is deposited on the surface of the sheet of fiber. Following the application of TWEEN® 20, the sheet of fiber is passed into a comb guide and then wound on a warp beam. A warp is a large wide cylinder onto which individual fibers are wound in parallel to provide a sheet of fibers. Next, warp beams are converted into a finished mesh fabric by means of interlocking knit loops. Eight warp beams are mounted in parallel onto tricot machine let-offs and fed into the knitting elements at a constant rate determined by the 'runner length'. Each individual monofilament fiber from each beam is fed through a series of dynamic tension elements down into the knitting 'guides'. Each fiber is passed through a single guide, which is fixed to a guide bar. The guide bar directs the fibers around the needles forming the mesh fabric structure. The mesh fabric is then pulled off the needles by the take down rollers at a constant rate of speed determined by the fabric 'quality'. The mesh fabric is then taken up and wound onto a roll.

After knitting or weaving, the PHA mesh, preferably a P4HB mesh, can be scoured with water to remove lubricants used in the knitting or weaving process, such as TWEEN® 20. The scoured mesh may optionally be further cleaned by treatment with other cleaning agents such as detergents. In a particularly preferred embodiment, the PHA mesh can be scoured ultrasonically with water.

After scouring, the PHA mesh, preferably a P4HB mesh, is optionally conditioned, for example, by heat setting. Benefits of conditioning include the relief of any stresses in the mesh that are induced during the mesh preparation process.

D. Calendering of PHA Meshes

PHA polymers and copolymers possess properties that are useful for preparing absorbable surgical meshes that can be calendered to provide thin meshes with low profiles, high burst strengths, and smoother surfaces. These calendered meshes are suitable for use in tissue reinforcement applications, and in particular for use in the surgical treatment of pelvic organ prolapse where meshes with smooth surfaces, high burst strength and thin profiles are particularly advantageous.

It has been discovered that surgical meshes made from PHA meshes, preferably meshes of P4HB and copolymers thereof, can be calendered to produce meshes with smooth surfaces and thinner profiles, without significant loss of burst strength or damage to the meshes. In particular, the orientation of P4HB fibers in a P4HB mesh is not lost during calendering. Thus, calendering does not result in loss of orientation of the oriented P4HB monofilament fibers in an oriented P4HB monofilament mesh. Furthermore, it has also been discovered that calendering of the surgical meshes of P4HB and copolymers thereof does not significantly reduce the pore sizes of the meshes, and therefore the ability of tissue to grow into the meshes is not perturbed. Calendering of the meshes made from P4HB and copolymers thereof using the conditions herein also results in little change to the stiffness of the meshes. This is also a key advantage of the new method since increased mesh stiffness can result in a more abrasive mesh, and prevent the mesh from contouring to tissue at the implantation site. A more abrasive mesh can easily cause tissue erosion, and result in a poor surgical outcome.

In a preferred embodiment, the PHA meshes, more specifically the P4HB meshes, can be calendered using a 2 roll calendering mill that applies pressure to the mesh and decreases the mesh thickness. In an alternative embodiment, the PHA meshes can be calendered using an alternative configuration of rollers provided that the rollers apply pressure to the mesh to decrease the mesh thickness. In a particularly preferred embodiment, a mesh of P4HB or copolymer therefore is calendered using a 2 roll calendering mill.

To calender a PHA mesh, more specifically a P4HB mesh, the mesh is fed between moving rollers. The thickness of the calendered mesh can be controlled by adjusting the nip gap. The nip gap is the distance between the rollers. Thinner meshes can be produced by moving the rollers closer together, and feeding the mesh between the nip gap. There is no specific limitation on the nip gap. It will depend on the target thickness of the calendered PHA mesh. In one embodiment, the nip gap distance is set to 0.1 mm±0.09 mm less than the desired thickness of the P4HB mesh.

In an embodiment, the thickness of the calendered PHA mesh, more specifically the P4HB mesh, is between 50 to 99%, more preferably 50% to 85%, and even more preferably 50% to 80% of the thickness of the mesh prior to calendering. The thickness of the calendered mesh can be 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 and 99% of the thickness of the mesh prior to calendering. In another embodiment, the thickness of the calendered mesh can be between 0.05 mm and 5 mm, more preferably between 0.1 mm and 1 mm, and even more preferably between 0.2 mm and 0.7 mm, including 0.1, 0.2, 0.3, 0.4, 0.5, 0.6, 0.7, 0.8, 0.9 and 1.0 mm.

In an embodiment, the pore size of the calendered PHA mesh, more specifically the P4HB mesh, is not less than 40%, more preferably not less than 30%, and even more preferably not less than 20% of the pore size of the mesh prior to calendering. The pore size of the mesh can be between 0.05 $mm^2$ and 10 $mm^2$, more preferably between 0.25 $mm^2$ and 8 $mm^2$, and even more preferably between 0.4 $mm^2$ and 6 $mm^2$, including 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, and 6.0 $mm^2$.

In an embodiment, the stiffness of the PHA mesh, more specifically the P4HB mesh, after calendering is between 0.01 N and 5 N, more preferably between 0.1 N and 2 N, and even more preferably between 0.4 N and 1.8 N, including 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9 and 2.0 N.

In an embodiment, the calendered PHA mesh, more specifically the P4HB mesh, has an areal density between 5 $gm/m^2$ and 250 $g/m^2$, more preferably between 10 $g/m^2$ and 100 $g/m^2$, and even more preferably between 40 $g/m^2$ and 100 $g/m^2$, including 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 $g/m^2$.

In an embodiment, the calendered PHA mesh, more specifically the P4HB mesh, has a surface area ratio between 0.5 $cm^2/cm^2$ and 5 $cm^2/cm^2$, and more preferably between 1 $cm^2/cm^2$ and 4 $cm^2/cm^2$, including 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 and 4.0 $cm^2/cm^2$.

In an embodiment, the calendered PHA mesh, more specifically the P4HB mesh, has a suture pullout strength between 1 N and 100 N, more preferably between 5 N and 50 N, and even more preferably between 7 N and 40 N, including 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40 N.

In an embodiment, the calendered PHA mesh, more specifically the P4HB mesh, has a burst strength not less than 80% of the burst strength of the surgical mesh prior to calendering. In an embodiment, the burst strength is between 30 N and 300 N, including between 30, 40, 50, 60, 70, 80, 90, 100, 110, 120, 130, 140, 150, 160, 170, 180, 190, 200, 210, 220, 230, 240, 250, 260, 270, 280, 290 and 300 N.

Calendering of the PHA meshes must be undertaken at temperatures lower that the melting points of the PHA polymers comprising the mesh. In the case of P4HB meshes, calendering is preferably performed at a temperature less than 55° C., more preferably less than 45° C., and even more preferably less than 30° C., but greater than 4° C. A particularly preferred temperature for calendering P4HB meshes and PHA meshes is ambient temperature. In one embodiment, different temperatures for calendering may be achieved by heating or cooling the rollers of the calendering mill.

In some embodiments, the mesh is calendered by applying heat at a temperature between 25° C. and 50° C. under a pressure of 1-100 pounds per linear inch of the mesh width.

In a preferred embodiment, the PHA mesh is calendered on both sides of the mesh. In another embodiment, the PHA mesh is calendered on one side of the mesh using a combination roller set. For example, the PHA mesh can be calendered on just one side of the mesh using one metal surfaced roller and one rubber surfaced roller. In another embodiment, the PHA mesh can be calendered using one or more rollers that are textured. For example, the PHA mesh can be fed between two textured rollers to produce a PHA mesh that is textured on both sides. Or in another alternative embodiment, the PHA mesh can be fed between one textured roll and one metal roller or rubber roller to produce a PHA mesh that is textured only on one side.

While it is preferable to scour the PHA mesh prior to calendering to remove lubricant, the mesh may in an alternative embodiment be scoured after calendering.

In an embodiment, the PHA mesh, preferably the P4HB mesh, can be washed after calendering, for example, with 70% aqueous alcohol.

In some embodiments, the PHA mesh can be further treated by heat setting the mesh, such as in hot water.

In another embodiment, a film may be attached to one side or both sides of the PHA mesh, preferably the P4HB mesh, prior to calendering, or after calendering, the mesh. The mesh, the film, or both the mesh and the film may be treated so that the film adheres to the mesh. The film may incorporate an additive, and may also be coated with a bioactive agent or incorporate a bioactive agent. In a preferred embodiment, P4HB film is attached to a P4HB mesh, and the composite of the P4HB film and mesh is calendered.

The calendered PHA meshes may be sterilized using ethylene oxide, gamma-irradiation, or electron beam radiation (e-beam). In a preferred embodiment, calendered P4HB surgical meshes are sterilized using ethylene oxide, and more preferably cold ethylene oxide.

E. Coating of Calendered PHA Meshes

In an embodiment, the PHA meshes, preferably the P4HB meshes, may be coated with other substances, such as additives and bioactive agents. The coatings may range from a thin coating on the surface of a PHA fiber, or more preferably a P4HB fiber, to complete coverage or encapsulation of a PHA mesh. The additives and bioactive agents may be applied directly or first suspended or dissolved in a carrier, such as another polymer. In a preferred embodiment, the PHA meshes comprise P4HB and may be coated with antimicrobial agents.

IV. Methods of Delivery of Calendered PHA Meshes

The calendered PHA meshes, preferably the P4HB calendered meshes, may be implanted using traditional open surgery techniques, and may also, if desired be implanted using minimally invasive techniques, for example, by laparoscopic surgery.

In a preferred embodiment, the PHA meshes, more preferably the P4HB meshes, are implanted using minimally invasive techniques when used for pelvic floor reconstruction, hernia repair, orthopedic repairs, mastopexy, and other plastic surgeries.

One skilled in the art will appreciate that these calendered PHA meshes can also be delivered by other minimally invasive methods as well as using more traditional open surgery techniques.

In some embodiments, the calendered PHA meshes can be used in surgeries such as breast lift, breast reconstruction, buttock lift, thigh lift, body lift, arm lift, tummy tuck, body contouring, facial reconstruction, forehead lift, brow lift, eyelid lift, facelift, rhytidectomy, rhinoplasty, neck lift, cosmetic repair, facial scar revision, treatment of urinary incontinence (SUI), urethral suspension, bladder repair, tissue engineering, guided tissue repair and regeneration, sling procedures, ligament repair, tendon repair, tendon augmentation, rotator cuff repair, osteochondral repair, controlled release, and drug delivery.

The present invention will be further understood by reference to the following non-limiting examples.

Example 1: Preparation of a Diamond Construction Calendered P4HB Mesh

A P4HB monofilament mesh with the Diamond construction shown in FIG. 1 was knit on a tricot machine with 32 courses per inch and 13 wales per inch from 100 μm diameter P4HB monofilament fiber, washed to remove lubricant, and heat set. The resulting pre-calendered mesh had the properties shown in Table 1. The mesh was then calendered using a 2 roll calendering mill at ambient temperature with a nip gap of 0.18 mm to yield a calendered P4HB monofilament mesh with a Diamond construction and the properties shown in Table 1. The example demonstrates that the P4HB mesh can be calendered to reduce its thickness by over 33%, yet only lose less than 7% of its burst strength, and retain almost the same pore size (2.24 mm for the mesh before calendering versus 2.22 mm for the mesh after calendering). Furthermore, calendering resulted in a decrease in stiffness of the mesh by about 18%.

TABLE 1

Properties of P4HB Monofilament Meshes with Different Constructions Before and After Calendering

| Mesh Construction | Fiber Diameter (micron) | Process | Thickness (mm) | Aerial Density (gms/m²) | Pore Size (mm²) | Surface Area Ratio (cm²/cm²) | Pliability/Stiffness (N) | Suture Pull-Out MD (N) | Suture Pull-Out CMD (N) | Tensile Strength MD (N) | Tensile Strength CMD (N) | Ball Burst Strength (N) |
|---|---|---|---|---|---|---|---|---|---|---|---|---|
| Diamond | 100 | Pre-Calendering | 0.42 | 49.50 | 2.24 | 1.60 | 0.73 | 19.74 | 22.47 | 25.50 | N/A | 119.39 |
| Diamond | 100 | Calendered | 0.28 | 49.70 | 2.22 | 1.60 | 0.60 | 20.67 | 24.12 | 29.42 | N/A | 111.25 |
| Diamond Plus | 100 | Pre-Calendering | 0.61 | 57.30 | 2.92 | 1.85 | 0.50 | 23.45 | 25.91 | 39.52 | 20.10 | 81.40 |
| Diamond Plus | 100 | Calendered | 0.34 | 74.40 | 2.46 | 2.40 | 0.44 | 19.71 | 26.78 | 47.46 | 23.34 | 86.30 |
| Crochet | 100 | Pre-Calendering | 0.49 | 47.80 | 4.25 | 1.54 | 0.58 | 9.79 | 27.97 | 51.78 | 9.41 | 77.00 |
| Crochet | 100 | Calendered | 0.26 | 57.70 | 3.61 | 1.86 | 0.60 | 13.50 | 30.56 | 52.17 | 13.34 | 69.23 |
| Delaware | 100 | Pre-Calendering | 0.51 | 84.96 | 0.42 | 2.74 | 1.73 | 28.09 | 47.62 | 68.94 | 67.86 | 210.58 |
| Delaware | 100 | Calendered | 0.41 | 94.80 | 0.40 | 3.06 | 1.79 | 28.88 | 42.42 | 81.10 | 76.59 | 215.65 |
| Marquisette | 100 | Pre-Calendering | 0.47 | 51.21 | 3.38 | 1.65 | 0.44 | 7.44 | 26.82 | 52.27 | 16.67 | 72.57 |
| Marquisette | 100 | Calendered | 0.29 | 60.55 | 3.38 | 1.95 | 0.66 | 13.30 | 23.75 | 37.56 | 17.75 | 80.67 |
| Marquisette Plus | 100 | Pre-Calendering | 0.45 | 64.52 | 2.07; 1.15 | 2.08 | 0.63 | 16.10 | 26.97 | 50.90 | 30.90 | 98.56 |
| Marquisette Plus | 100 | Calendered | 0.29 | 70.35 | 1.67; 0.81 | 2.27 | 0.94 | 21.57 | 24.54 | 48.35 | 40.01 | 106.01 |
| Marlex | 100 | Pre-Calendering | 0.38 | 48.52 | 0.45; 0.17 | 1.57 | 0.73 | 15.74 | 15.74 | 27.85 | 19.91 | 106.33 |
| Marlex | 100 | Calendered | 0.23 | 49.30 | 0.49; 0.09 | 1.59 | 0.69 | 23.94 | 24.18 | 19.61 | 20.59 | 104.47 |

Example 2: Preparation of a Diamond Plus Construction Calendered P4HB Mesh

A P4HB monofilament mesh with the Diamond Plus construction shown in FIG. 1 was knit on a tricot machine with 23 courses per inch and 13 wales per inch from 100 μm diameter P4HB monofilament fiber, washed to remove lubricant, and heat set. The resulting pre-calendered mesh had the properties shown in Table 1. The mesh was then calendered using a 2 roll calendering mill at ambient temperature with a nip gap of 0.24 mm to yield a calendered P4HB monofilament mesh with a Diamond Plus construction and the properties shown in Table 1. The example demonstrates that the P4HB mesh can be calendered to reduce its thickness by over 44%. In this example, calendering results in a small increase in burst strength, and a small reduction in pore size of less than 16%.

Example 3: Preparation of a Crochet Construction Calendered P4HB Mesh

A P4HB monofilament mesh with the Crochet construction shown in FIG. 1 was knit on a crotchet machine with 32 courses per inch and 11 wales per inch from 100 μm diameter P4HB monofilament fiber, washed to remove lubricant, and heat set. The resulting pre-calendered mesh had the properties shown in Table 1. The mesh was then calendered using a 2 roll calendering mill at ambient temperature with a nip gap of 0.16 mm to yield a calendered P4HB monofilament mesh with a Crotchet construction and the properties shown in Table 1. The example demonstrates that the P4HB mesh can be calendered to reduce its thickness by 47% with a loss of only about 10% of its burst strength, virtually no change in stiffness, and a reduction in pore size of just 15%.

Example 4: Preparation of a Delaware Construction Calendered P4HB Mesh

A P4HB monofilament mesh with the Delaware construction shown in FIG. 1 was knit on a tricot machine with 27 courses per inch and 14 wales per inch from 100 μm diameter P4HB monofilament fiber, washed to remove lubricant, and heat set. The resulting pre-calendered mesh had the properties shown in Table 1. The mesh was then calendered using a 2 roll calendering mill at ambient temperature with a nip gap of 0.31 mm to yield a calendered P4HB monofilament mesh with a Delaware construction and the properties shown in Table 1. The example demonstrates that the thickness of the mesh can be reduced by 20% with no loss in burst strength (a slight increase was discovered), and only a 5% reduction in pore size.

Example 5: Preparation of a Marquisette Construction Calendered P4HB Mesh

A P4HB monofilament mesh with the Marquisette construction shown in FIG. 1 was knit on a crotchet machine with 34 courses per inch and 11 wales per inch from 100 μm diameter P4HB monofilament fiber, washed to remove lubricant, and heat set. The resulting pre-calendered mesh had the properties shown in Table 1. The mesh was then calendered using a 2 roll calendering mill at ambient temperature with a nip gap of 0.19 mm to yield a calendered P4HB monofilament mesh with a Marquisette construction and the properties shown in Table 1. The example demonstrates that the P4HB mesh can be calendered to reduce its thickness by 38% with no loss of burst strength (an 11% increase in burst strength was discovered), and no change in pore size.

Example 6: Preparation of a Marquisette Plus Construction Calendered P4HB Mesh A P4HB monofilament mesh with the Marquisette Plus construction shown in FIG. 1 was knit on a crotchet machine with 34 courses per inch and 11 wales per inch from 100 μm diameter P4HB monofilament fiber, washed to remove lubricant, and heat set. The resulting pre-calendered mesh had the properties shown in Table 1. The mesh was then calendered using a 2 roll calendering mill at ambient temperature with a nip gap of 0.19 mm to yield a calendered P4HB monofilament mesh with a Marquisette Plus construction and the properties shown in Table 1. The example demonstrates that the thickness of the P4HB mesh can be reduced by over 35% with no loss of burst strength (a 7% increase in burst strength was discovered).

Example 7: Preparation of a Marlex Construction Calendered P4HB Mesh

A P4HB monofilament mesh with the Marlex construction shown in FIG. 1 was knit on a tricot machine with 41 courses per inch and 18 wales per inch from 100 μm diameter P4HB monofilament fiber, washed to remove lubricant, and heat set. The resulting pre-calendered mesh had the properties shown in Table 1. The mesh was then calendered using a 2 roll calendering mill at ambient temperature with a nip gap of 0.13 mm to yield a calendered P4HB monofilament mesh with a Marlex construction and the properties shown in Table 1. The example demonstrates that the thickness of the mesh can be reduced by 39% with virtually no loss of burst strength (less than 2%), and little change in stiffness.

We claim:

1. A calendered surgical mesh comprising monofilament fiber of a poly-4-hydroxybutyrate homopolymer or copolymer thereof, wherein the calendered mesh has a pore size not less than 40% of the pore size of the mesh prior to calendering.

2. The calendered surgical mesh of claim 1, wherein the mesh is knit or woven.

3. The calendered surgical mesh of claim 1, wherein the fiber is oriented.

4. The calendered surgical mesh of claim 1, wherein the mesh is resorbable.

5. The calendered surgical mesh of claim 1, wherein the mesh is: (i) three-dimensional and can be temporarily deformed for implantation, (ii) contoured to fit a patient's tissue, or (iii) shaped into a plug.

6. The calendered surgical mesh of claim 1, wherein the mesh can be deformed for placement in a patient by a minimally invasive method.

7. The calendered surgical mesh of claim 1, further comprising a bioactive agent or additive.

8. The calendered surgical mesh of claim 7, wherein the bioactive agent is an antimicrobial agent selected from the following group: rifampin; minocycline and its hydrochloride, sulfate, or phosphate salt; triclosan; chlorhexidine; vancomycin and its hydrochloride, sulfate, or phosphate salt; tetracycline and its hydrochloride, sulfate, or phosphate salt, and derivatives; gentamycin; cephalosporin antimicrobials; aztreonam; cefotetan and its disodium salt; loracarbef; cefoxitin and its sodium salt; cefazolin and its sodium salt; cefaclor; ceftibuten and its sodium salt; ceftizoxime; ceftizoxime sodium salt; cefoperazone and its sodium salt; cefuroxime and its sodium salt; cefuroxime axetil; cefprozil; ceftazidime; cefotaxime and its sodium salt; cefadroxil; ceftazidime and its sodium salt; cephalexin; cefamandole nafate; cefepime and its hydrochloride, sulfate, and phosphate salt; cefdinir and its sodium salt; ceftriaxone and its sodium salt; cefixime and its sodium salt; cefpodoxime proxetil; meropenem and its sodium salt; imipenem and its sodium salt; cilastatin and its sodium salt; azithromycin; clarithromycin; dirithromycin; erythromycin and hydrochloride, sulfate, or phosphate salts, ethylsuccinate, and stearate forms thereof, clindamycin; clindamycin hydrochloride, sulfate, or phosphate salt; lincomycin and hydrochloride, sulfate, or phosphate salt thereof, tobramycin and its hydrochloride, sulfate, or phosphate salt; streptomycin and its hydrochloride, sulfate, or phosphate salt; neomycin and its hydrochloride, sulfate, or phosphate salt; acetyl sulfisoxazole; colistimethate and its sodium salt; quinupristin; dalfopristin; amoxicillin; ampicillin and its sodium salt; clavulanic acid and its sodium or potassium salt; penicillin G; penicillin G benzathine, or procaine salt; penicillin G sodium or potassium salt; carbenicillin and its disodium or indanyl disodium salt; piperacillin and its sodium salt; ticarcillin and its disodium salt; sulbactam and its sodium salt; moxifloxacin; ciprofloxacin; ofloxacin; levofloxacins; norfloxacin; gatifloxacin; trovafloxacin mesylate; alatrofloxacin mesylate; trimethoprim; sulfamethoxazole; demeclocycline and its hydrochloride, sulfate, or phosphate salt; doxycycline and its hydrochloride, sulfate, or phosphate salt; oxytetracycline and its hydrochloride, sulfate, or phosphate salt; chlortetracycline and its hydrochloride, sulfate, or phosphate salt; metronidazole; dapsone; atovaquone; rifabutin; linezolide; polymyxin B and its hydrochloride, sulfate, or phosphate salt; sulfacetamide and its sodium salt; clarithromycin; and silver ions, salts, and complexes.

9. The calendered surgical mesh of claim 1, wherein the monofilament fiber comprises poly-4-hydroxybutyrate homopolymer.

10. The calendered surgical mesh of claim 9, wherein the calendered mesh has one or more of the following properties: (i) a burst strength not less than 80% of the burst strength of the surgical mesh prior to calendering; (ii) a burst strength between 30 N and 300 N measured by test method ASTM D6797-02 "Standard test method for bursting strength of fabrics constant rate of extension (CRE) ball burst test," using a MTS Q-Test Elite universal testing machine or similar device and a testing fixture with a ⅜-inch diameter ball, (iii) a thickness between 50 to 99% of the mesh prior to calendering (iv) a thickness between 0.05 mm and 5 mm, (v) a pore size not less than 30% of the pore size of the mesh prior to calendering, (vi) a pore size between 0.05 mm$^2$ and 10 mm$^2$, (vii) a suture pullout strength between 1 N and 100 N, (viii) a stiffness between 0.01 N and 5 N, (ix) an areal density between 5 gm/m$^2$ and 250 g/m$^2$, (x) a surface area ratio between 0.5 cm$^2$/cm$^2$ and 5 cm$^2$/cm$^2$, and (xi) oriented fibers, wherein the fibers have been stretched 6-11X their unoriented length.

11. The calendered surgical mesh of claim 10, wherein the mesh has a thickness between 0.1 mm and 1 mm.

12. The calendered surgical mesh of claim 10, wherein the mesh has a pore size not less than 20% of the pore size of the mesh prior to calendering.

13. A method of forming the calendered surgical mesh of claim 1, the method comprising the steps of: knitting or weaving a mesh, and calendering the mesh in order to reduce the thickness of the mesh.

14. The method of claim 13, wherein the mesh is calendered by heating the mesh under pressure.

15. The method of claim 14, wherein the mesh is heated to a temperature between 25° C. and 50° C. under a pressure of 1-100 pounds per linear inch of the mesh width.

16. The method of claim 13, further comprising one or more of the following steps: (i) heat setting the mesh, (ii)

washing the mesh with an alcoholic solution, or (iii) sterilizing the mesh with ethylene oxide, electron beam irradiation or gamma-irradiation.

17. The method of claim 13, wherein the mesh is formed from monofilament fiber with one or more of the following properties: (i) diameter between 20 μm and 900 μm, (ii) tensile strength between 100 MPa and 1,500 MPa, (iii) tensile modulus between 70 MPa and 2 GPa, (iv) elongation to break between 10% and 1100%, and (v) polymer or copolymer weight average molecular weight between 50 kDa and 1,200 kDa.

18. A method of using the calendered surgical mesh of claim 1, wherein the calendered surgical mesh is implanted in a patient' body.

19. The method of claim 18, wherein the calendered surgical mesh is implanted by a minimally invasive method.

20. The method of claim 19, where the calendered surgical mesh is implanted laparoscopically for repair of a hernia, a breast lift, or pelvic organ prolapse.

* * * * *

UNITED STATES PATENT AND TRADEMARK OFFICE
CERTIFICATE OF CORRECTION

PATENT NO. : 10,874,498 B2
APPLICATION NO. : 16/122305
DATED : December 29, 2020
INVENTOR(S) : Said Rizk et al.

It is certified that error appears in the above-identified patent and that said Letters Patent is hereby corrected as shown below:

In the Specification

Column 1, Line 53, replace "calendaring" with --calendering--.
Column 7, Lines 54-55, replace "dimeth ylformamide" with --dimethylformamide--.
Column 12, Lines 38-39, replace "0.4 mm$^2$ and 6 mm$^2$" with --0.04 mm$^2$ and 6 mm$^2$--.
Column 12, Lines 52-53, replace "5 gm/m$^2$ and 250 g/m$^2$" with "5 g/m$^2$ and 250 g/m$^2$--.
Column 15, Table 1, in the heading, replace "Aerial" with --Areal--.

In the Claims

Claim 18, Column 19, Line 14, replace "patient' body" with --patient's body--.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*